United States Patent
Blakley (10) Patent No.: US 6,813,928 B2
(45) Date of Patent: Nov. 9, 2004

(54) SENSOR SYSTEM AND METHOD EMPLOYING SHARED TRANSDUCER ELEMENTS

(75) Inventor: Daniel Robert Blakley, Philomath, OR (US)

(73) Assignee: Hewlett-Packard Development, L.P., Houston, TX (US)

( * ) Notice: Subject to any disclaimer, the term of this patent is extended or adjusted under 35 U.S.C. 154(b) by 52 days.

(21) Appl. No.: 10/356,084

(22) Filed: Jan. 31, 2003

(65) Prior Publication Data

US 2004/0149040 A1 Aug. 5, 2004

(51) Int. Cl.[7] .......................... G01N 29/02; G01N 29/22
(52) U.S. Cl. ..................... 73/19.03; 73/32 A; 73/64.53; 310/313 R
(58) Field of Search .................. 73/19.03, 24.01–24.06, 73/31.05, 31.06, 32 A, 54.24, 54.27, 61.49, 61.75, 61.79, 64.53, 625, 626, 627; 310/313 A, 313 B, 313 C, 313 D, 313 R (56) References Cited

U.S. PATENT DOCUMENTS

| | | | |
|---|---|---|---|
| 3,582,838 A | * | 6/1971 | DeVries ...................... 333/194 |
| 3,983,424 A | * | 9/1976 | Parks ..................... 310/313 B |
| 4,055,072 A | * | 10/1977 | Fletcher et al. ............ 73/24.01 |
| 5,448,126 A | * | 9/1995 | Eda et al. ................ 313/313 A |
| 5,477,098 A | * | 12/1995 | Eguchi et al. .......... 310/313 R |
| 6,144,332 A | * | 11/2000 | Reindl et al. ................. 342/42 |
| 2002/0011761 A1 | * | 1/2002 | Takeuchi et al. ........ 310/313 B |

FOREIGN PATENT DOCUMENTS

JP       55040967 A   *   3/1980            G01D/5/56

* cited by examiner

Primary Examiner—Hezron Williams
Assistant Examiner—Rose M. Miller (57) ABSTRACT

A transducer-based sensor system including a first transducer system and a second transducer system spaced from the first transducer system so as to define a sample area between the first transducer system and the second transducer system where the first transducer system and second transducer system are collectively configured to transmit surface acoustic waves in multiple directions through the sample area and receive such surface acoustic waves.

25 Claims, 5 Drawing Sheets

SENSOR SYSTEM AND METHOD EMPLOYING SHARED TRANSDUCER ELEMENTS

BACKGROUND

Transducer devices are commonly used as sensors in various settings. Transducer-based sensors may be used, for example, in rupture event scanning (RES) applications. RES technology involves using mechanical energy to break bonds within a sample material. In such a setting, transducers may be employed to produce the mechanical energy that breaks the bonds (e.g., by applying voltages to a piezoelectric material), and to sense and analyze phenomena occurring as a result of a rupture event within the sample material.

Transducer-based sensor systems such as those described above typically employ multiple distinct transducer elements to perform the functions described above. This allows for larger samples to be tested, and allows distinct portions of a sample material to be individually tested. Indeed, it is often desirable to employ a large number of transducer elements within a limited physical area, and/or to increase the density of transducer elements within a sensor device.

Many existing systems suffer from limitations that may render those systems undesirable for use in particular applications. For example, many existing transducer systems employ transducer elements in topologies that are relatively inefficient in terms of the physical space occupied by the system. Some topologies require relatively complicated supporting components to drive the transducers and process outputs. Still other systems are substantially limited in the rate at which sample data may be processed.

SUMMARY

A transducer-based sensor system including a first transducer system and a second transducer system spaced from the first transducer system so as to define a sample area between the first transducer system and the second transducer system where the first transducer system and second transducer system are collectively configured to transmit surface acoustic waves in multiple directions through the sample area and receive such surface acoustic waves.

DETAILED DESCRIPTION

Figures 1, 2, 3:
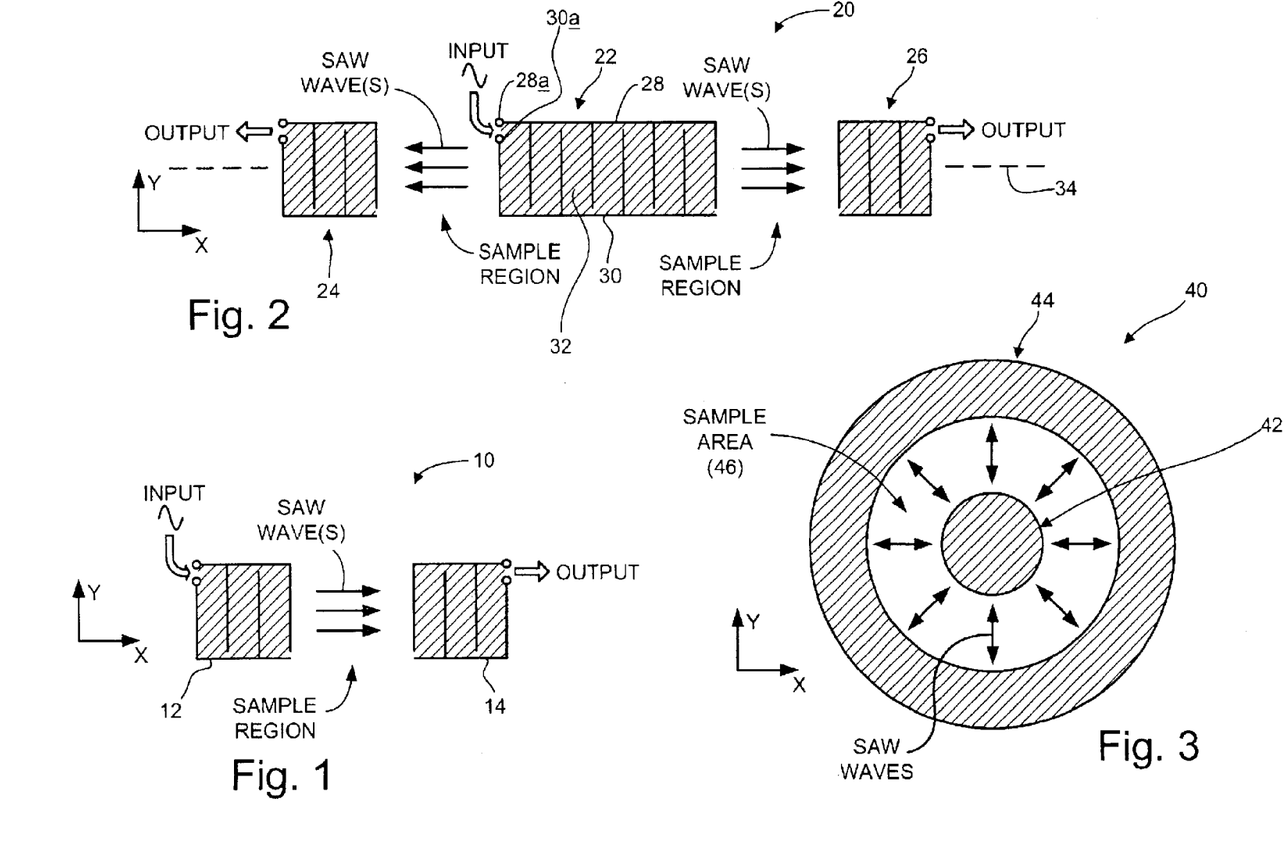
FIG. 1 schematically depicts a surface acoustic wave (SAW) device.
FIG. 2 schematically depicts a SAW device having a shared transducer element configuration.
FIG. 3 schematically depicts a SAW device having a radial configuration.

The following description addresses systems, devices and methods that employ transducer devices in connection with surface acoustic wave (SAW) technology. FIG. 1 depicts a transducer-based sensor system including an exemplary surface acoustic wave (SAW) device 10. Device 10 includes a transmitter transducer element 12 and a receiver transducer element 14. The transducer elements are configured to transmit and receive SAW waves, respectively, that propagate through a sample region, as indicated in the figure. Typically, a sample material is disposed within the sample region, and the SAW waves are analyzed at receiver element 14 to obtain information about the material within the sample region.

Typically, transmitter 12 and receiver 14 are formed in an interdigitated construction, in which piezoelectric material is interposed between conductive electrodes. In response to application of an input signal across the electrodes of transmitter 12, such as the depicted sinusoidal input signal, the piezoelectric material of the transmitter vibrates or otherwise moves. This generates SAW waves which propagate through the sample region and impinge upon receiver 14. At receiver 14, the impinging waves cause the piezoelectric material of the receiver to move, which in turn produces an output voltage across the receiver electrodes.

FIG. 2 depicts another transducer-based sensor system including an exemplary surface acoustic wave (SAW) device 20. Device 20 includes an emitter or transmitter 22, and two receivers 24 and 26. Receiver 24 and 26 may share transmitter 22, as explained in more detail below. Similar to the transducer elements of FIG. 1, transmitter 22 and receivers 24 and 26 typically are transducer devices constructed at least partially from material having piezoelectric properties. Between the transmitter and each receiver is a sample region, in which a sample material may be placed, such as a biological sample to be tested.

As shown, an input signal such as a sinusoidally-varying voltage may be applied to electrodes 28 and 30 of transmitter 22, via terminals 28a and 30a. The applied voltage produces vibration or other movement of piezoelectric material 32 disposed between the electrodes. This movement produces surface acoustic waves which propagate through the sample regions. In the depicted device, the SAW waves typically propagate in a single direction (e.g., back and forth parallel to axis 34.)

After propagating through the sample regions, the transmitted SAW waves impinge upon receivers 24 and 26. Receivers 24 and 26 typically are transducer devices constructed from pairs of electrodes with interposed piezoelectric material, similar to transmitter 22. Accordingly, the Impinging waves cause the piezoelectric material at the receivers to move, which in turn produces a voltage on the receiver electrodes. As shown, output signals may be obtained from the electrode terminals of receivers 24 and 26.

The transmitters and receivers described above may be referred to as transducer elements, or transmitter elements and receiver elements depending on how the elements are deployed. As used herein, "element" refers to a transducer device constructed from a pair of electrodes that interact with piezoelectric material. Transmitter elements and receiver elements will often be very similar in construction, though they may be configured to perform different functions when deployed in the described systems and methods. Specifically, transmitter elements respond to electrical inputs by producing mechanical movements as outputs. In the described examples, these movements produce surface acoustic waves. In contrast, the receiver elements are subjected to externally-applied forces. These forces commonly are produced by surface acoustic waves impinging upon the piezoelectric material of the receiver element. The forces cause the piezoelectric material to move, which in turn affects the voltage residing across the electrodes of the receiver element. The voltage across the electrodes is the output, and may be accessed via the electrode terminals of the receiver element.

In addition to classing transducer elements according to function, transducer elements may be referred to differently depending on their location within a described system. For example, as will be discussed in more detail, FIG. 2 depicts a non-radial device having a central transducer system and a peripheral transducer system. Transducer elements within the central transducer system may be referred to as central transducer elements, or simply central elements. Similarly, transducer elements within the periphery may be referred to as peripheral transducer elements or peripheral elements.

The sample material through which the waves propagate typically will have various effects upon the waves. These effects can be analyzed by studying the output signals produced by receivers 24 and 26, for example by comparing the output signals to the sinusoid used to drive transmitter 22. This analysis can yield valuable information about the sample material, such as information about chemical bonds existing within the material and rupture events caused by propagation of the waves through the sample.

As indicated above, the transmitter and receiver elements are constructed at least partially from a piezoelectric material. It will be appreciated that any suitable piezoelectric material may be used in these constructions. In many cases, it will be desirable to form the piezoelectric material in a particular orientation, such as in the intended direction of wave propagation. For example, the piezoelectric material in device 20 typically is a crystalline-type material oriented along the X-axis, such that most or all of the piezoelectric movement (e.g., expansion and contraction due to impinging waves or applied voltages) occurs along the X-axis (e.g., axis 34).

The transmitter and receiver elements shown in FIGS. 1 and 2 may be formed in an interdigitated configuration. Referring particularly to transmitter 22 (FIG. 2), electrode 28 has a plurality of downward extending fingers which interleave and alternate with corresponding upward-extending fingers of electrode 30. As shown, the piezoelectric material may be provided in sections disposed between the fingers. Typically, the interposed sections of piezoelectric material are uniformly spaced from section to section.

For a given sinusoidal input, the vibrational frequency of transmitter 22 is dependent upon the dimensions of the individual sections of piezoelectric material. Referring to the depicted example, the vibrational frequency for a given input will vary with the X-axis spacing of the individual interdigitated finger sections of piezoelectric material. As indicated above, the spacing of the electrode fingers often is constant, though variable spacing may be employed.

In addition, it should be appreciated that different modes of operation may be employed in connection with the depicted device. For example, surface skimming acoustic waves may be used, and/or bulk-wave and Love-wave modes of operation may be employed.

The various transducer systems described herein may be implemented to provide for SAW wave propagation in multiple directions, rather than simply along or parallel to a single axis. In such implementations, the transmitter and receiver elements may be oriented in different ways to allow for propagation in multiple directions.

For example, FIG. 3 schematically depicts a transducer device 40 having a radial configuration. In certain environments, use of such a radial design may improve the efficiency with which physical space is used. As shown, device 40 may include a central transducer system 42 and a peripheral transducer system 44 disposed in a radial configuration about the central transducer system. Typically, the central and peripheral systems are situated and spaced apart so that a sample area 46 surrounds the central transducer system 42 and is situated between the central transducer system and the peripheral transducer system. Central transducer system 42 includes one or more transducer elements, as described below, including one or more receiver elements and/or one or more transmitter elements. Likewise, peripheral transducer system 44 typically has one or more transducer elements, including one or more receiver elements and/or one or more transmitter elements.

Regardless of the specific topology that is employed, device 40 typically is configured to produce surface acoustic waves that propagate in multiple directions (e.g., radially) through sample area 46 between the peripheral and central transducer systems. As indicated by the arrows in FIG. 3, SAW waves may be generated to propagate in virtually any direction within sample area 46.

From the above, it should be appreciated that many different configurations are possible for central transducer system 42 and peripheral transducer system 44. In some configurations, it will be desirable that the central transducer system and peripheral transducer system contain equal numbers of transducer elements, with the transmitter elements and receiver elements being in one-to-one correspondence. Typically, in such a configuration, a given transmitter element generates surface acoustic waves such that the waves propagate through sample area 46 and impinge upon a receiver element that corresponds only to that transmitter element. Alternatively, the central transducer system and the peripheral transducer system may have varying numbers of transducer elements, with one transmitter being shared by several receivers, or vice versa.

FIGS. 4A, 4B, 4C, 5A, 5B and 5C show exemplary implementations of SAW device 40, each having a different alternate configuration for central transducer system 42 and peripheral transducer system 44. In all of the examples, central transducer system 42 may contain transmitter elements configured to transmit SAW waves outward through sample area 46 for reception by receiver elements at peripheral system 44. Alternatively, the transmitters may be at the periphery, with generated waves propagating inward to receiver elements within the central transducer system. Furthermore, either or both of the central and peripheral systems may include both transmitter and receiver elements.

Figure 4A:
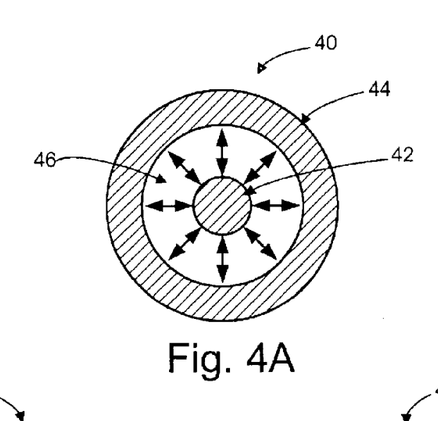
FIGS. 4A, 4B, 4C, 5A, 5B and 5C depict alternate configurations of the radial SAW device shown in FIG. 3.
Figure 4B:
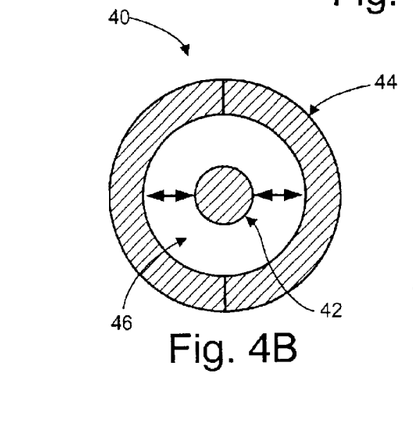
Figure 4C:
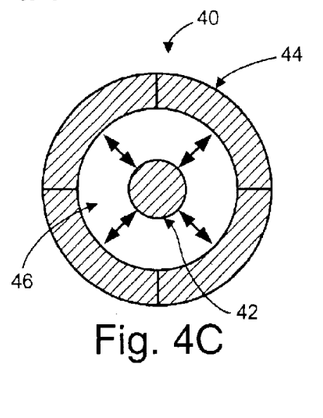

Referring specifically to FIG. 4A, central transducer system 42 and peripheral transducer system 44 have only one transducer element each. In FIG. 4B, central transducer system 42 has one transducer element, while the periphery contains two elements. In FIG. 4C, the center has a single transducer element, while the periphery has four transducer elements.

Figure 5A:
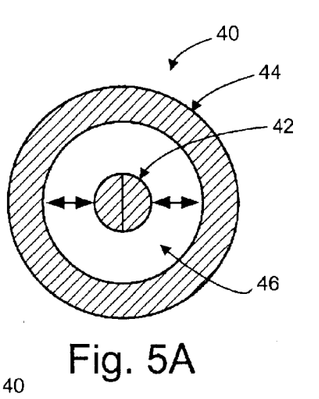
Figure 5B:
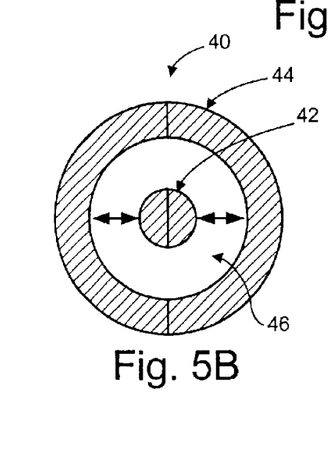
Figure 5C:
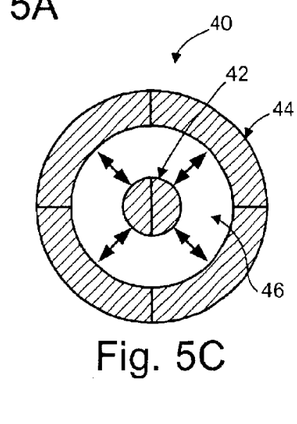

In FIG. 5A, central transducer system 42 has two transducer elements, while peripheral transducer system 44 has one transducer element. In FIG. 5B, both the central transducer system 42 and peripheral transducer system 44 have two transducer elements. In FIG. 5C, central transducer system 42 has two transducer elements, while peripheral transducer system 44 has four transducer elements. From the above, it should be appreciated that central transducer system 42 and peripheral transducer system 44 may contain any practicable number of elements, as desired and appropriate for a given application. Also, the center may transmit SAW waves for reception at the periphery in response to applied input drive signals, or vice versa.

In many cases it will be desirable to have shared configuration for the transducer elements. For example, a single transmitter element may be shared by multiple receiver elements. Such an arrangement could be implemented in connection with the device of FIG. 4B, for example, in which two peripheral receivers receive SAW waves generated by a single central transmitter. As another example, referring to FIG. 5A, a single peripheral transmitter could transmit waves for reception at two central receiver elements. Many different sharing combinations are possible. As explained below, sharing (e.g., a single transmitter with multiple receivers, or vice versa) can reduce the physical size of the transducer array and simplify circuitry needed to support the transducer elements.

Figure 6:
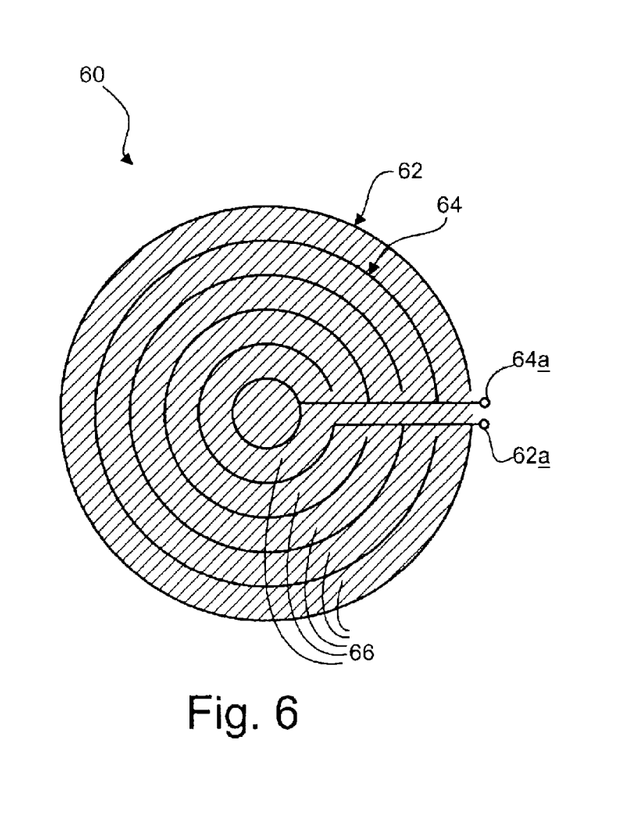
FIG. 6 depicts an embodiment of a central transducer element that may be employed in connection with the radial SAW device shown in FIG. 3.
Figure 7:
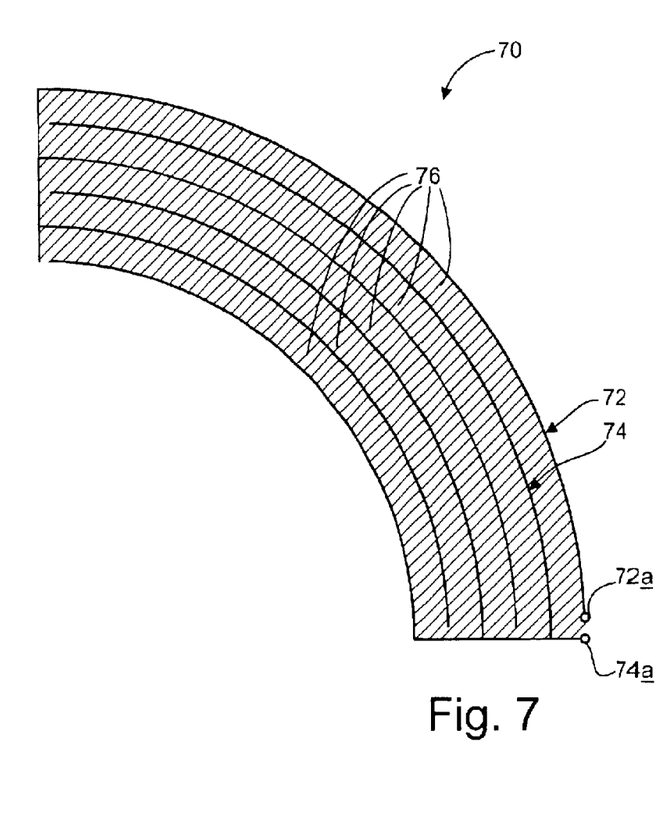
FIG. 7 depicts an embodiment of a peripheral transducer element that may be employed in connection with the radial SAW device shown in FIG. 3.

FIGS. 6 and 7 show examples of transducer elements that may be used in an exemplary configuration where four peripheral elements share one central element. Referring first to FIG. 6, a central transducer element 60 is depicted. Central transducer element 60 may be provided as part of central transducer system 42 (FIG. 3). As shown, central transducer element 60 may be formed from a pair of electrodes 62 and 64. Each electrode may include plural arcuate fingers that are interdigitated in an alternating fashion with corresponding arcuate fingers of the other electrode, as shown. Sections 66 of piezoelectric material may be disposed between the fingers, similar to the linear devices described with reference to FIGS. 1 and 2, but in an arcuate configuration. Typically, the piezoelectric sections are uniformly spaced, though it may be desirable in some cases to have variable spacing.

Central transducer element 60 may be implemented as a transmitter element or as a receiver element. When used as a transmitter, input drive signals may be applied at electrode terminals 62a and 64a. The potential across the piezoelectric material causes the piezoelectric material to move, thereby generating surface acoustic waves. In some cases, it will be desirable to fabricate the piezoelectric material so that its crystalline structure is oriented along radial lines extending outward from the center of transducer element 60 (e.g., radially outward from central transducer system 42 of FIG. 3). This may facilitate wave propagation in a radial outward direction from the center of transducer element (e.g., radially outward through sample area 46 shown in FIG. 3). It should be appreciated, however, that the piezoelectric material may be provided in non-radial orientations.

When element 60 is implemented as a receiver, the element typically operates in a reverse fashion. Specifically, impinging surface acoustic waves (e.g., propagating radially inward through sample area 46) produce an output voltage signal at terminals 62a and 64a. In any case, it should be appreciated that element 60 is configured to accommodate radial wave propagation, rather than simply linear propagation along a single axis.

Turning now to FIG. 7, a peripheral transducer element 70 is depicted. Peripheral transducer system 44 (FIG. 3) may include four elements similar to element 70, disposed in a radial configuration around central transducer element 60 (FIG. 6). Similar to central transducer element 60, peripheral transducer element may be formed in an arcuate construction, with arcuate interdigitated electrodes 72 and 74, and interposed sections 76 of piezoelectric material. Output and input signals may be received from or applied to electrode terminals 72a and 74a. Similar to central transducer element 60, peripheral transducer element 70 may be implemented as a transmitter element or receiver element.

Figure 8:
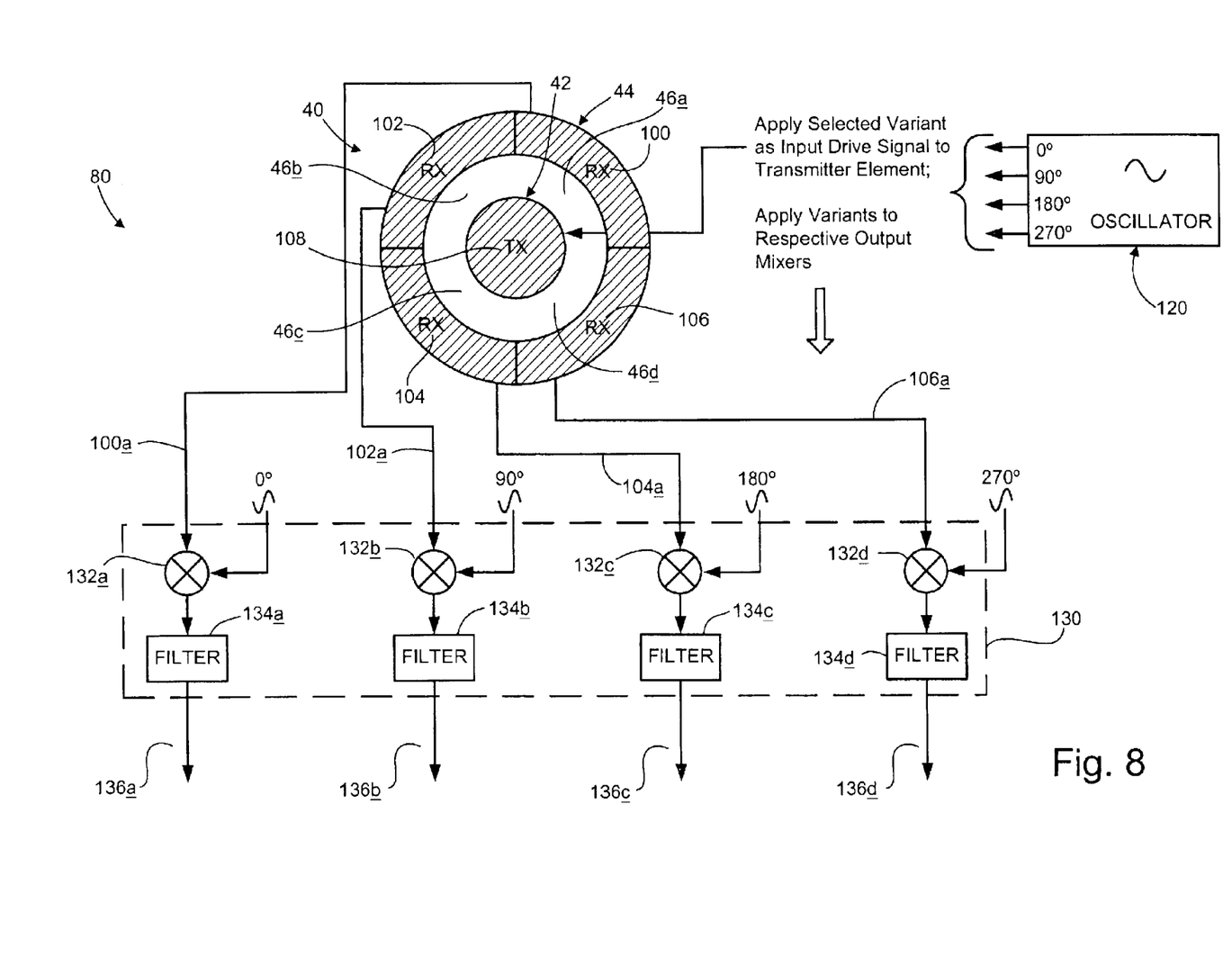
FIG. 8 depicts a transducer-based sensor system, including an alternate implementation of the radial SAW device shown in FIG. 3.

FIG. 8 depicts a transducer-based sensor system 80. As shown, sensor system 80 may employ a radial SAW device 40, as discussed above, in which four peripheral transducer elements are radially disposed about a shared central element. Specifically, peripheral transducer system 44 includes four receiver (RX) elements 100, 102, 104 and 106. The receiver elements are radially disposed about central transducer system 42, which includes a single transmitter element 108. Transmitter (TX) element 108 may be constructed similar to the element shown in FIG. 6, and receiver elements may be constructed similar to the element shown in FIG. 7.

System 80 may also include a drive signal generator 120 operatively coupled to transmitter element 42a. In addition, an output processing subsystem 130 may be coupled to receiver elements 100, 102, 104 and 106. Drive signal generator 120 may be configured to apply an input drive signal to transmitter element 108. Transmitter element 108, in response, produces surface acoustic waves that propagate radially outward through sample area 46 and impinge upon the receiver elements. The receiver elements produce output signals which may be processed by output processing subsystem 110 in order to obtain information about matter disposed within the sample area.

The depicted exemplary configuration allows sample area 46 to be tested within four discrete sub-areas, also referred to as sampling locations: (1) 46a, between transmitter element 108 and receiver element 100, (2) 46b, between transmitter element 108 and receiver element 102, (3) 46c, between transmitter element 108 and receiver element 104, and (4) 46d, between transmitter element 108 and receiver element 106. It should be appreciated that any practicable number of sub-areas may be tested, by using different numbers of transmitter and receiver elements. In addition, constraining or guiding SAW waves to particular sections within sample area 46 may be facilitated via various structures, and/or via use of Love-wave techniques and modes of operation.

The depicted example is advantageous, in that it allows four different sample sites to be tested with less accompanying circuitry than required in prior system. In particular, use of a shared transmitter element with multiple receiver elements can substantially reduce the amount of supporting circuitry needed, such as multiplexing circuitry for selecting between transducer elements. In addition, in many applications, the depicted radial configuration may be packed more efficiently than other topologies of transducer elements. This can be a substantial benefit in applications where physical space is at a premium, or where it is important to maximize sensor density.

Referring still to FIG. 8, output processing subsystem 130 may include, for each receiver element, a corresponding mixer section (132a, 132b, 132c, and 132d, respectively) and a filter (134a, 134b, 134c, and 134d, respectively). Output from the filters may be obtained on output lines 136a, 136b, 136c and 136d, respectively.

Though depicted as separate devices, the individual mixer devices may be collectively referred to as a mixer, and the individual filter devices may be referred to as a filter. Indeed, the individual devices may be consolidated into one or more single components configured to process multiple signals. As explained in detail below, these components may be employed to detect and isolate desired signals, and/or eliminate noise and other undesired signals.

The filters may be implemented in a variety of configurations, including configurations incorporating passive and/or active filter components. Filtering may be achieved using a passive RC network, for example. Additionally, or alternatively, active components such as a digital signal processor may be employed to provide filtering. Filtering may be performed based on frequency and/or phase of incoming signals. Indeed, in some embodiments, a digital signal processor is employed to perform linear phase processing, so as to allow for rejection of unwanted signal components. To achieve the desired signal isolation, the digital signal processor may be configured to subtract, for a given transducer output, any out-of-phase, steady-state components. In many cases, frequency filtering using linear-phase topologies or algorithms facilitates channel separation and helps to preserve resultant pulse characteristics. Additionally, in order to achieve adjacent signal rejection in a system employing four simultaneously active channels, it will often be desirable to limit phase deviation of the filter to ±45°.

In typical modes of operation, the depicted exemplary system will be operated so that outputs for the receiver elements are obtained sequentially through use of output processing subsystem 130. To facilitate selection of active receiver element, drive signal generator 120 may be configured to use different drive signal variants to drive transmitter element 108. In the depicted example, a different variant is used for each receiver element. Specifically, as shown, four different phase-shifted variants of a local oscillator may be employed: (1) a first variant shifted in phase by 0° from the local oscillator; (2) a second variant shifted in phase by 90° from the local oscillator; (3) a third variant shifted in phase by 180° from the local oscillator; and (4) a fourth variant shifted in phase by 270° from the local oscillator. Although phase offsets have proved effective, different types of drive signal variation may be employed.

Each drive signal variant corresponds to one of the receiver elements. For example, to obtain output corresponding to receiver element 102, the 90° variant is applied as a drive signal to transmitter element 108. This would produce SAW waves propagating outward through sample area 46, and would typically result in those waves impinging on all four of the receiver elements. Therefore, all four receiver elements would produce output signals (e.g., on output lines 100a, 102a, 104a and 106a). However, the same drive signal variant (e.g., the 90° variant) may be applied to the mixer section corresponding to selected receiver element, or mixer section 132b.

Use of the same variant that is used to drive the transmitter element may be referred to as a "synchronous" deployment within output processing subsystem 130, since the variant typically is in sync with the desired signal components residing on line 102a. The mixing at section 132b creates sum frequencies and difference frequencies, which are selectively filtered using filter 134b. The resulting signal on output line 136b therefore corresponds to the particular portion, or sampling location 46b of sample area 46 between the transmitter element 108 and the selected receiver element (i.e., receiver element 102).

Because the mixer sections corresponding to the unselected receiver elements are fed with signal variants other than the 90° variant used to drive the transmitter element (e.g., the 0°, 180° and 270° variants), any outputs arising on lines 136a, 136c and 136d typically are substantially attenuated by the corresponding mixers and filters, and the only substantial output is that corresponding to the selected receiver element 102. To select a different receiver element, a different one of the drive signal variants is employed to drive transmitter element 108. In the depicted example, the 0° variant selects receiver element 100 and sub-area 46a, the 90° variant selects receiver element 102 and sub-area 46b, the 180° variant selects receiver element 104 and sub-area 46c, and the 270° variant selects receiver element 106 and sub-area 46d. The above process of selecting desired components and rejecting undesired components may be referred to as synchronous detection.

Typically, as in the above example, each sampling location has a corresponding unique drive signal, or variant (e.g., a variant that can be distinguished from those used for the other sampling locations). This produces a characteristic response for that sampling location, allowing that response to be readily identified and separated from undesired signal components through various techniques, such as filtering and the like.

It should be further understood that that the detection/selection capability discussed above may be performed in many different ways. Drive signal variations other than phase offsets may be employed, such as variations in frequency, amplitude, waveform type, etc. Indeed, the description should be understood to encompass use of any type of drive signal variations that facilitate separating desired output components for a specific sampling location from undesired components.

In addition to or instead of the synchronous detection described above, the receiver element outputs may be gated with logic circuitry to select the desired receiver element.

From the above, it should be understood that each sub-area (sampling location) of sample area 46 has a corresponding drive signal variant, a corresponding pair of transducer elements, and a corresponding output channel in output processing subsystem 130. For example, for sub-area 46a, the corresponding drive signal variant is the 0° variant, the corresponding transducer elements are transmitter element 108 and receiver element 100, and the corresponding output channel is defined by mixer section 132a and filter 134a. For sub-area 46b, the corresponding drive signal variant is the 90° variant, the corresponding transducer elements are transmitter element 108 and receiver element 102, and the corresponding output channel is defined by mixer section 132b and filter 134b, and so on for the other sub-areas.

Figure 9:
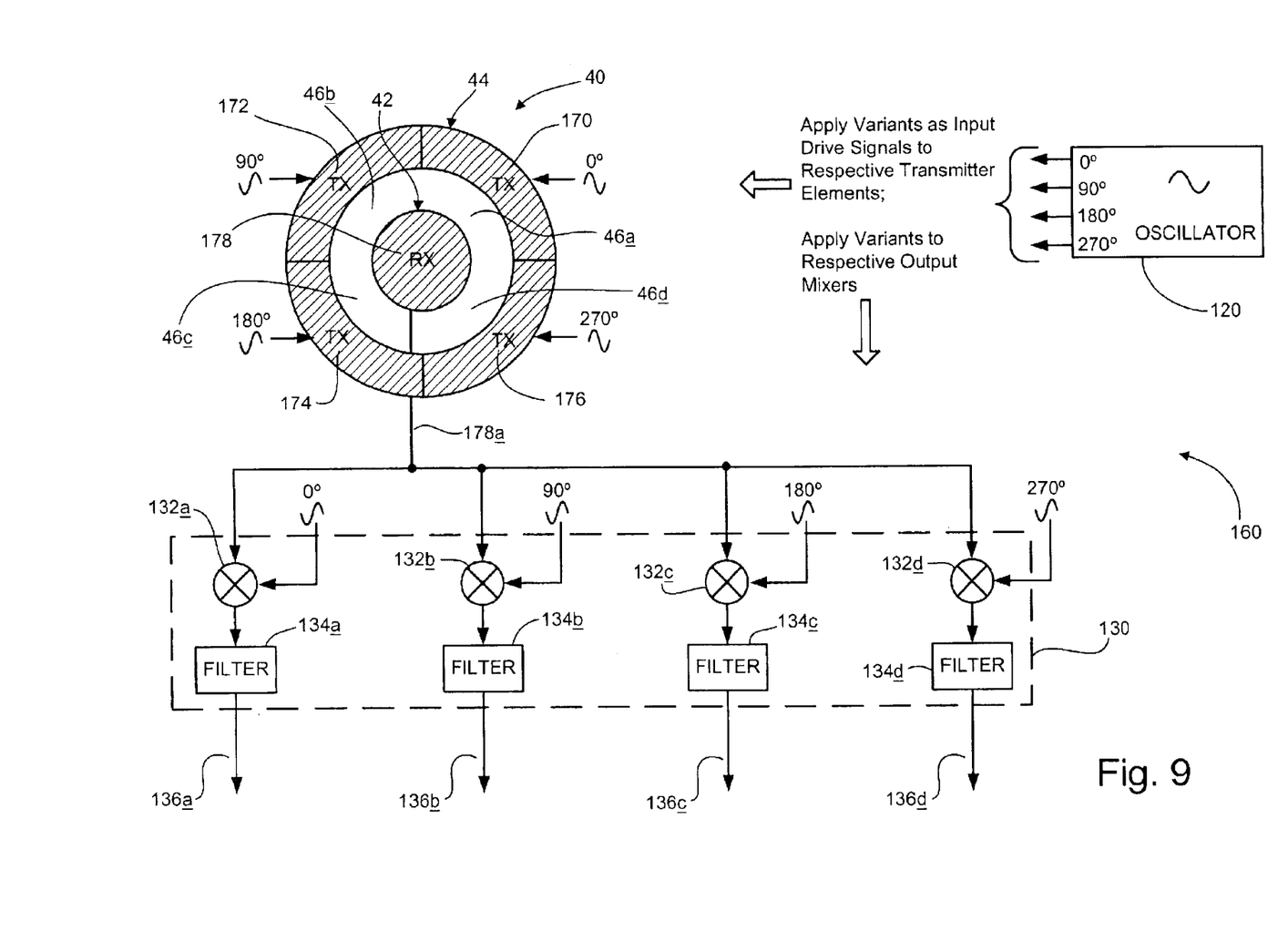
FIG. 9 depicts another transducer-based sensor system, including another alternate implementation of the radial SAW device shown in FIG. 3.

FIG. 9 depicts another embodiment 160 of a transducer-based sensor system. Similar to the embodiment of FIG. 8, sensor system 160 may include a radial SAW device 40, as discussed above, with a peripheral transducer system 44 radially disposed about a sample area and a central transducer system 42. In contrast to the previous embodiment, waves are transmitted from peripheral transducer system 44 to central transducer system 42. Specifically, in the depicted example, peripheral transducer system 44 includes four transmitter elements 170, 172, 174 and 176. The transmitter elements are radially disposed about central transducer system 42, which includes a single receiver element 178. The different transducer elements may be provided with the arcuate construction discussed with reference to FIGS. 6 and 7.

Drive signal generator 120 may be operatively coupled to transmitter elements 170, 172, 174 and 176. Output processing subsystem 130 may be coupled to receiver element 178. As in the previous embodiment, drive signal generator 130 may be configured to apply drive signals to radial SAW device 40 (i.e., to transmitters 170, 172, 174 and 176 in the depicted example). This results in SAW waves propagating inward in a radial direction toward receiver element 178. The impinging waves cause output signals to be produced by receiver element (e.g., on output line 178a), which may then be processed by output processing subsystem 130.

As with the previously described embodiment, the depicted system allows sample area 46 (FIG. 3) to be tested within four discrete locations or regions: 46a, 46b, 46c and 46d. The depicted exemplary embodiment may also be implemented to provide the advantages described above relating to efficient use of physical space and simplification of supporting circuitry.

Referring still to FIG. 9, drive signal generator 120 typically is configured to apply different drive signal variants to the transmitter elements of radial SAW device 40. For example, the depicted generator is configured to produce variants of an oscillatory signal that are respectively shifted in phase by 0°, 90°, 180° and 270° from the base oscillatory signal. As indicated, the 0° variant may be applied to transmitter element 170, the 90° variant may be applied to transmitter element 172, the 180° variant may be applied to transmitter element 174 and the 270° variant may be applied to transmitter element 176.

Receiver element 178 typically is coupled to various components provided within output processing subsystem 130. Specifically, as in the previous example, output processing subsystem 130 may include, for each of the four testable sub-areas of sample area 46, a corresponding mixer section (132a, 132b, 132c and 132d, respectively) and a filter (134a, 134b, 134c and 134d, respectively). Outputs for the specific sub-areas of sample area 46 may be obtained on output lines 136a, 136b, 136c and 136d. As indicated, the mixer sections may be fed with the drive signal variants from drive signal generator 120. Specifically, as indicated, the 0° variant may be applied to mixer section 132a, the 90° variant may be applied to mixer section 132b, the 180° variant may be applied to mixer section 132c and the 270° variant may be applied to mixer section 132d. Output from receiver element 178 may be mixed with the drive signal variants to provide a synchronous detection capability similar to that described above. In particular, the mixing may facilitate selection of desired components simultaneously residing on output line 178a, may aid in selecting signals corresponding to a desired sub-area within sample area 46, and/or may aid in rejecting or inhibiting noise and other undesired signal components.

System 160 may be operated sequentially, in which data is obtained for only one sub-area of sample area 46 at a time. For example, drive signal generator 120 may be operated to stimulate only one of the transmitter elements at a time.

Alternatively, it will be desirable in some cases to operate all of the transmitter elements simultaneously. This can improve processing times, in that simultaneous operation allows all sub-areas 46a, 46b, 46c and 46d of sample area 46 to be tested at the same time. During simultaneous operation, a number of different signal components typically will be residing on receiver element output line 178a. However, the SAW waves in the example emanate from transmitter elements that are being driven by different drive signal variants. Accordingly, the SAW waves propagating through the different sub-areas of sample area 46 will have different characteristics (e.g., phase offsets), allowing them to be discriminated from one another.

The differences in the SAW waves in turn will typically cause receiver element 178 to output multiple signal components on output line 178a. Desired components may be obtained using synchronous detection and filtering, as described above. For example, because the 0° variant is used at mixer section 132a, the signal on output line 136a will substantially correspond only to sub-area 46a of sample area 46. The signal corresponding to this sub-area is selected through operation of mixer section 132a and filter 134a, and signal components corresponding to other sub-areas are attenuated and not passed through on output line 136a, because they are out of sync with the 0° variant. Similarly, the output on line 136b corresponds to sub-area 46b, the output on line 136c corresponds to sub-area 46c, and the output on line 136d corresponds to sub-area 46d.

As with the previous embodiment, it should be understood that each sub-area has a corresponding drive signal variant, a corresponding pair of transducer elements, and a corresponding output channel in output processing subsystem 130. For sub-area 46a, the corresponding drive signal variant is the 0° variant, the corresponding transducer elements are transmitter element 170 and receiver element 178, and the corresponding output channel is defined by mixer section 132a and filter 134a, and so on for the other sub-areas.

The embodiments of FIGS. 8 and 9 both employ a SAW device having a shared, or common transmitter element that acts as a transmitter or receiver relative to multiple distributed transducer elements. FIG. 2 also shows use of a shared element (e.g., a single transmitter element shared by two receiver elements). It should be understood that many different combinations and topologies are possible in configurations having a shared element. A single common element may be shared among any practicable number of distributed elements. The SAW device may be operated sequentially, such that outputs for given sampling locations are obtained individually, or the device may be operated simultaneously, as described above with reference to FIG. 9. Furthermore, shared elements may be employed in configurations other than the radial topology discussed with reference to SAW device 40. Also, in many cases it will be desirable to construct a sensor system as an array of SAW devices (e.g., an array of SAW devices 40).

It should also be appreciated that the sensor devices described herein may be implemented in non-shared configurations. For example, SAW device 40 (FIG. 3) may be implemented with transmitter elements and receiver elements in one-to-one correspondence. FIGS. 4A and 5B depict examples of such an implementation.

The description herein further encompasses a method of obtaining sample data using SAW waves. The method first includes applying drive signals to a SAW device. The SAW device may be constructed according to any of the embodiments in the above description. Indeed, the SAW device typically will be constructed with a number of transducer elements, and a sharing configuration will often be employed, where a shared transducer element is shared by N distributed transducer elements. The shared element and distributed elements typically are arranged to define N sampling locations (e.g., sub-areas 46a, 46b, 46c and 46d in FIG. 8) respectively positioned between the shared element and the individual distributed elements.

The method further includes producing surface acoustic waves within the SAW device, in response to the applied drive signals. As in the embodiments discussed above, the waves are produced to propagate through the N sampling locations. The waves impinge upon one or more of the transducer elements, such that the SAW device produces output. The method further includes receiving this output and employing synchronous detection to obtain desired individual outputs for each of the N sampling locations.

While the present embodiments and method implementations have been particularly shown and described, those skilled in the art will understand that many variations may be made therein without departing from the spirit and scope defined in the following claims. The description should be understood to include all novel and non-obvious combinations of elements described herein, and claims may be presented in this or a later application to any novel and non-obvious combination of these elements. Where the claims recite "a" or "a first" element or the equivalent thereof, such claims should be understood to include incorporation of one or more such elements, neither requiring nor excluding two or more such elements.

What is claimed is:

1. A transducer-based sensor system, comprising:
   a central transducer system including a shared transducer element;
   a peripheral transducer system disposed radially about the central transducer system and including N distributed transducer elements;
   a sample area at least partially surrounding the central transducer system and disposed between the central transducer system and the peripheral transducer system so as to define N sampling locations, each sampling location being disposed between the shared transducer element and one of the distributed transducer elements, where the distributed transducer elements are transmitter elements configured to transmit surface acoustic waves radially through the sample area and where the shared transducer element is a receiver element configured to receive such surface acoustic waves; and
   a drive signal generator coupled with the transmitter elements and configured to drive the transmitter elements, where the drive signal generator is configured to simultaneously apply different drive signals to each of the transmitter elements.

2. The system of claim 1, where the different drive signals are variants of a base oscillator signal.

3. The system of claim 2, where the peripheral transducer system includes four transmitter elements, and where the drive signal generator is configured to simultaneously drive the four transmitter elements with oscillatory signals shifted in phase from the base oscillator signal by 0°, 90°, 180° and 270°, respectively.

4. The system of claim 1, further comprising an output processing subsystem operatively coupled with the receiver element, where the output processing subsystem is configured to process output received from the receiver element and, during such processing, use the different drive signals from the drive signal generator to synchronously detect individual output signals for the N sampling locations.

5. The system of claim 1, further comprising an output processing subsystem operatively coupled to at least one of the transducer elements, where the output processing subsystem is configured to extract, using synchronous detection, individual output signals corresponding to each of the N sampling locations.

6. The system of claim 5, where the drive signal generator and output processing subsystem are configured so that each of the different drive signals corresponds to a selected one of the N sampling locations and is used to synchronously detect output for the corresponding sampling location.

7. The system of claim 6, where the different drive signals are phase-shifted variants of a base oscillator signal.

8. The system of claim 1, where each of the shared transducer element and distributed transducer elements includes arcuate electrodes with piezoelectric material disposed between the arcuate electrodes.

9. A transducer-based sensor system, comprising
   a surface acoustic wave device, including:
      a shared transducer element; and
      N distributed transducer elements, where the shared transducer element and distributed transducer elements are positioned so as to define N sampling locations configured to accommodate passage of surface acoustic waves therethrough, each sampling location being disposed between the shared transducer element and one of the distributed transducer elements;
   a drive signal generator coupled to the surface acoustic wave device, where the drive signal generator is configured to apply drive signals to the surface acoustic wave device in order to produce surface acoustic waves within the surface acoustic wave device; and
   an output processing subsystem coupled to the surface acoustic wave device, where the output processing subsystem is configured to employ synchronous detection to selectively obtain individual output signals corresponding to each of the N sampling locations.

10. The system of claim 9, where the surface acoustic wave device has a non-radial configuration.

11. The system of claim 9, where the surface acoustic wave device has a radial configuration, in which the N distributed transducer elements are radially distributed about the shared transducer element, which is positioned in a central location.

12. The system of claim 11, where the shared transducer element is a transmitter element and the N distributed transducer elements are receiver elements, such that the shared transducer element is configured to transmit surface acoustic waves outward toward the N distributed transducer elements so that such surface acoustic waves impinge upon the N distributed transducer elements.

13. The system of claim 11, where the shared transducer element is a receiver element and the N distributed transducer elements are transmitter elements, such that the N distributed transducer elements are configured to transmit surface acoustic waves inward toward the shared transducer element so that such surface acoustic waves impinge upon the shared transducer element.

14. The system of claim 13, where the drive signal generator is configured to simultaneously apply different drive signals to each of the transmitter elements.

15. The system of claim 14, where the different drive signals are variants of a base oscillator signal.

16. The system of claim 15, where the N distributed transducer elements include four transmitter elements, and where the drive signal generator is configured to simultaneously drive the four transmitter elements with oscillatory signals shifted in phase from the base oscillator signal by 0°, 90°, 180° and 270°, respectively.

17. The system of claim 14, where the output processing subsystem is configured to process output received from the receiver element and, during such processing, use the different drive signals from the drive signal generator to synchronously detect individual output signals for the N sampling locations.

18. The system of claim 11, where each of the transducer elements includes arcuate electrodes with piezoelectric material disposed between the arcuate electrodes.

19. A transducer-based method for obtaining data from a sample using surface acoustic wave technology, the method comprising:

applying drive signals to a surface acoustic wave device having a plurality of transducer elements, where such transducer elements include:
a shared transducer element; and
N distributed transducer elements, where the shared transducer element and distributed transducer elements are positioned so as to define N sampling locations adapted to accommodate passage of surface acoustic waves therethrough, each sampling location being disposed between the shared transducer element and one of the distributed transducer elements;
producing surface acoustic waves in response to the drive signals so that the surface acoustic waves propagate through the sampling locations;
receiving output from the surface acoustic wave device, where such output arises from the surface acoustic waves impinging upon at least one of the transducer elements within the surface acoustic wave device; and
employing synchronous detection in connection with the output received from the surface acoustic wave device, in order to obtain individual output signals corresponding to each of the N sampling locations.

20. The method of claim 19, where applying drive signals to the surface acoustic wave device includes applying a different drive signal for each of the N sampling locations.

21. The method of claim 20, where employing synchronous detection includes, for a given one of the N sampling locations, using the drive signal corresponding to such sampling location to synchronously detect the individual output signal corresponding to such sampling location.

22. A transducer-based sensor system, comprising
a surface acoustic wave device, including:
a shared transducer means; and
N distributed transducer means, where the shared transducer means and distributed transducer means are positioned so as to define N sampling locations configured to accommodate passage of surface acoustic waves therethrough, each sampling location being disposed between the shared transducer means and one of the distributed transducer means;
drive signal generator means for applying drive signals to the surface acoustic wave device so as to produce surface acoustic waves within the surface acoustic wave device; and
an output processing subsystem coupled to the surface acoustic wave device, where the output processing subsystem includes means for employing synchronous detection to selectively obtain individual output signals corresponding to each of the N sampling locations.

23. A transducer-based sensor system, comprising:
a first transducer system;
a second transducer system spaced from the first transducer system so as to define a sample area between the first transducer system and the second transducer system,
where the first transducer system and second transducer system are collectively configured to transmit surface acoustic waves in multiple directions through the sample area and receive such surface acoustic waves; and
a drive signal generator coupled with a plurality of transmitter elements in one of the first transducer system and the second transducer system, where the drive signal generator is configured to simultaneously apply different drive signals to each of the transmitter elements.

24. The transducer-based sensor system of claim 23, where the first transducer system is centrally positioned, and where the second transducer system is disposed in a peripheral configuration about the central transducer system.

25. The transducer-based sensor system of claim 24, where the first and second transducer systems are configured to transmit surface acoustic waves radially through the sample area and receive such surface acoustic waves.

* * * * *